United States Patent [19]
Schwartz

[11] Patent Number: 6,056,692
[45] Date of Patent: May 2, 2000

[54] APPARATUS AND METHOD FOR LOCATING AND MARKING BLOOD VESSELS

[76] Inventor: John Q. Schwartz, 633 East Rd. 100 S., Monroe, Ind. 46772

[21] Appl. No.: 09/112,272

[22] Filed: Jul. 8, 1998

[51] Int. Cl.[7] ....................................................... A61B 8/00
[52] U.S. Cl. .......................... 600/443; 600/447; 600/459; 600/445
[58] Field of Search ........................... 600/443, 444–446, 600/447, 459, 454, 462, 463–467; 601/2; 606/169

[56] References Cited

U.S. PATENT DOCUMENTS

| | | |
|---|---|---|
| 4,457,311 | 7/1984 | Sorenson et al. .................... 600/447 |
| 5,010,890 | 4/1991 | Pfohl et al. . |
| 5,080,103 | 1/1992 | Olivier . |
| 5,080,104 | 1/1992 | Marks et al. . |
| 5,131,394 | 7/1992 | Gehlbach . |
| 5,148,809 | 9/1992 | Biegeleisen-Knight et al. . |
| 5,167,165 | 12/1992 | Brucher et al. ........................ 600/445 |
| 5,309,915 | 5/1994 | Ember . |
| 5,557,681 | 9/1996 | Thomasson . |
| 5,676,689 | 10/1997 | Kensey et al. . |
| 5,678,555 | 10/1997 | O'Connell . |
| 5,865,748 | 2/1999 | Co et al. .............................. 600/439 |

Primary Examiner—Marvin M. Lateef
Assistant Examiner—Ali M. Imam
Attorney, Agent, or Firm—Chase & Yakimo, L.C.

[57] ABSTRACT

A device for non-invasively locating and marking blood carrying vessels in a live human body includes a housing having a control panel for user selection of functions, a central processing unit controlling said functions. The device includes motorized legs for regulating the height of the housing above a patient's skin according to data received from a proximity sensor. The device includes an upper carriage driven in a first direction and a lower carriage driven in a second direction that is perpendicular to the first direction. The lower carriage is coupled to the upper carriage such that the lower carriage can be positioned at any position within an x-y plane. The device further includes a transducer for locating the position of a blood vessel through the transmission and receipt of ultrasonic waves. The transducer is mounted to the lower carriage such that the path of a blood vessel can be tracked through carriage movements according to signals received by the transducer. When a vessel has been located, the vessel is tracked and the x-y coordinates are stored in sequential memory locations. The x-y coordinates are then used by a plotter attached to the lower carriage to mark the path of the vessel upon the skin of the patient.

20 Claims, 11 Drawing Sheets

APPARATUS AND METHOD FOR LOCATING AND MARKING BLOOD VESSELS

BACKGROUND OF THE INVENTION

This invention relates to an improved device and method for locating and marking blood vessels in a body and, more particularly, to a self-contained, portable device which non-invasively locates vessels and visually marks the skin accordingly.

One of the most frequently performed medical procedures is the insertion of a needle into a live human body for the purpose of drawing blood, inserting a catheter, performing diagnostic tests, etc. Despite the frequency with which this task is undertaken, accurate insertion of a needle is often difficult where the position of the desired vessel is not readily apparent or where the vessel is very small. This difficulty often results in several unsuccessful attempts to penetrate the desired vessel—a result which obviously increases the discomfort experienced by the patient.

Several devices for locating blood vessels in a live human body have been proposed in the prior art, reference being made to U.S. Pat. No. 5,678,555 and the patents discussed therein. The devices described in the referenced patents transmit and receive ultrasonic or infrared signals to locate the position of a blood vessel. The system proposed in the '555 patent further provides for marking the skin immediately covering the detected vessel. The system, however, requires the use of several electronic components for locating and then temporarily marking the skin. It should also be noted that the accuracy of the prior art devices is partially dependent upon the steadiness of the medical personnel in moving and positioning the monitoring or marking equipment.

Although assumably effective in operation, none of the devices proposed in the prior art provides a completely self-contained, portable device which non-invasively locates and automatically marks the position of a blood vessel. It is thus desirable to have a single device with all of the above described advantages. It is further desirable to have such a device which can locate and mark vessels while remaining in a fixed position (e.g., about a patient's arm).

SUMMARY OF THE INVENTION

Accordingly, it is a general object of this invention to provide an improved device for locating and marking the position of blood carrying vessels in a live human body.

Another object of this invention is to provide an improved device, as aforesaid, which can remain in a fixed position while locating and marking the position of a blood vessel.

A particular object of this invention is to provide an improved device, as aforesaid, having carriages which can move within an x-y plane for locating and marking blood vessels.

Still another object of this invention is to provide an improved device, as aforesaid, which is easily movable from one location on a patient to another location or to another patient.

Yet another object of this invention is to provide an improved device, as aforesaid, which is non-invasive to the body of the patient.

A further object of this invention is to provide an improved device, as aforesaid, which includes all components within a single housing which are necessary for locating and marking blood vessels.

A still further object of this invention is to provide an improved device, as aforesaid, which can mark blood vessels using more than one color of ink to thereby minimize confusion regarding the path of a vessel.

Another particular object of this invention is to provide an improved device, as aforesaid, which can be adjusted to a desired distance from a patient's skin.

Other objects and advantages of this invention will become apparent from the following description taken in connection with the accompanying drawings, wherein is set forth by way of illustration and example, a now preferred embodiment of this invention.

The foregoing objects are attained by providing an improved device and method for locating and marking the position of blood carrying vessels in a live human body. The device includes a housing having a control panel for user selection of functions. The control panel is linked to a central processing unit (CPU) which controls user selected functions. The housing further includes threaded legs for regulating the distance between the housing and a patient's skin. At the user's request, the CPU can activate motors for screwably adjusting the height of the housing according to data received from a proximity sensor.

The device includes a transducer assembly which utilizes ultrasound or infrared signals to determine the precise position of a blood vessel. The transducer is attached to the underside of a lower carriage assembly which is in turn linked to an upper carriage assembly. Each carriage assembly is mounted to a threaded shaft and driven by stepping motors. The upper carriage is driven in a first direction while the lower carriage is driven in a second direction perpendicular to the first direction. The CPU can activate either or both of the shafts according to the signals received from the transducer. Accordingly, the lower carriage assembly may be positioned at any location within an x-y plane defined by the boundaries of the housing.

When the position of a vessel has been positively identified by the transducer, the CPU will cause the carriage assemblies to move along the path of the vessel, continually adjusting the position of the carriage assemblies according to the data received from the transducer. The x-y coordinates corresponding to the path of the vessel are stored in a memory location. When the set of coordinates defining a blood vessel have been stored, the sensing function is complete. Upon user request, the stored coordinates may be transmitted to a buffer in a plotter which can then plot the path and dimensions of the vessel on the skin of the patient. The plotter is attached to the underside of the lower carriage and can thus be positioned in the x-y plane as described above.

DESCRIPTION OF THE PREFERRED EMBODIMENT

Figure 1:
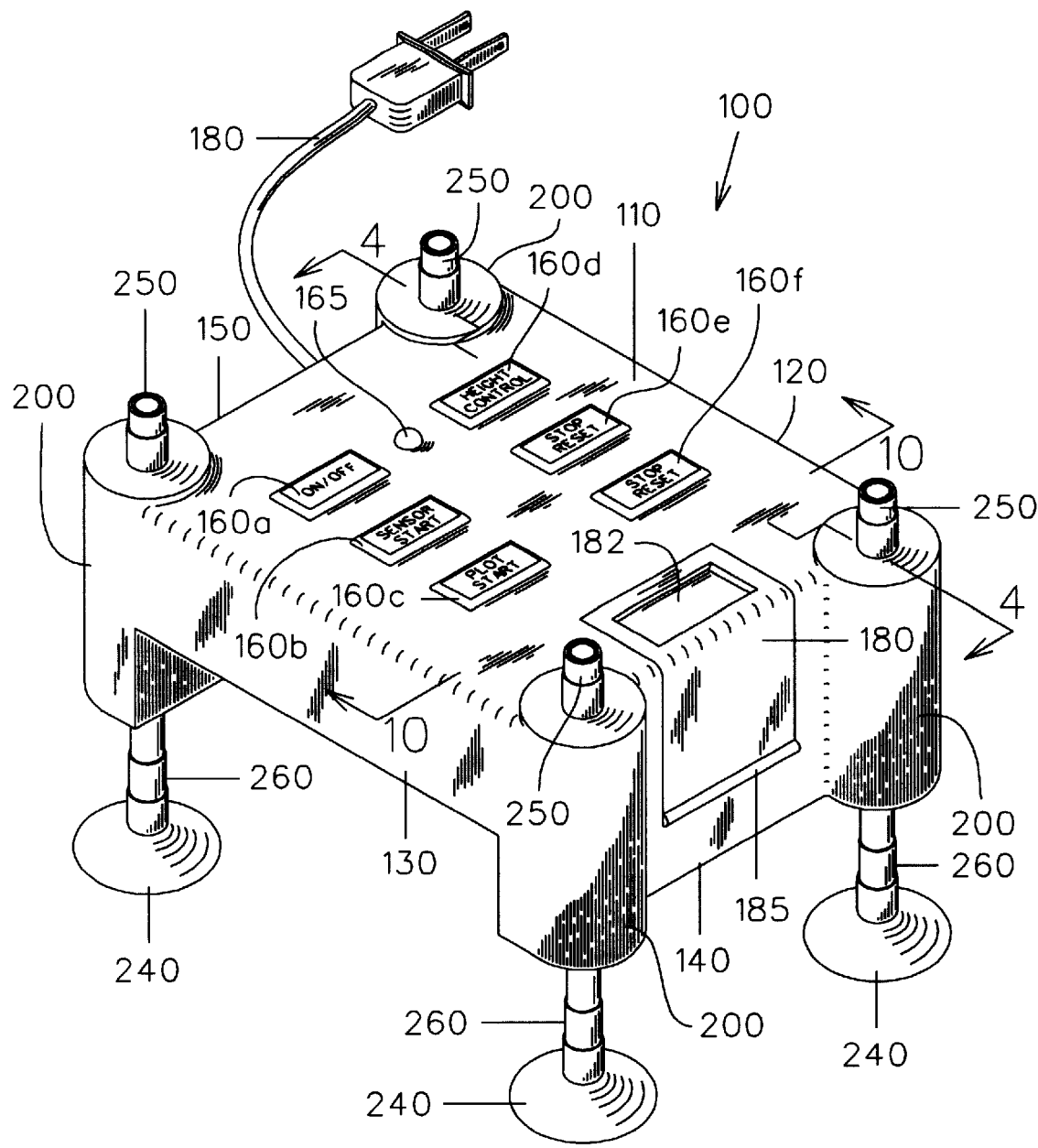
FIG. 1 is a perspective view of the device of the present invention.
Figure 2:
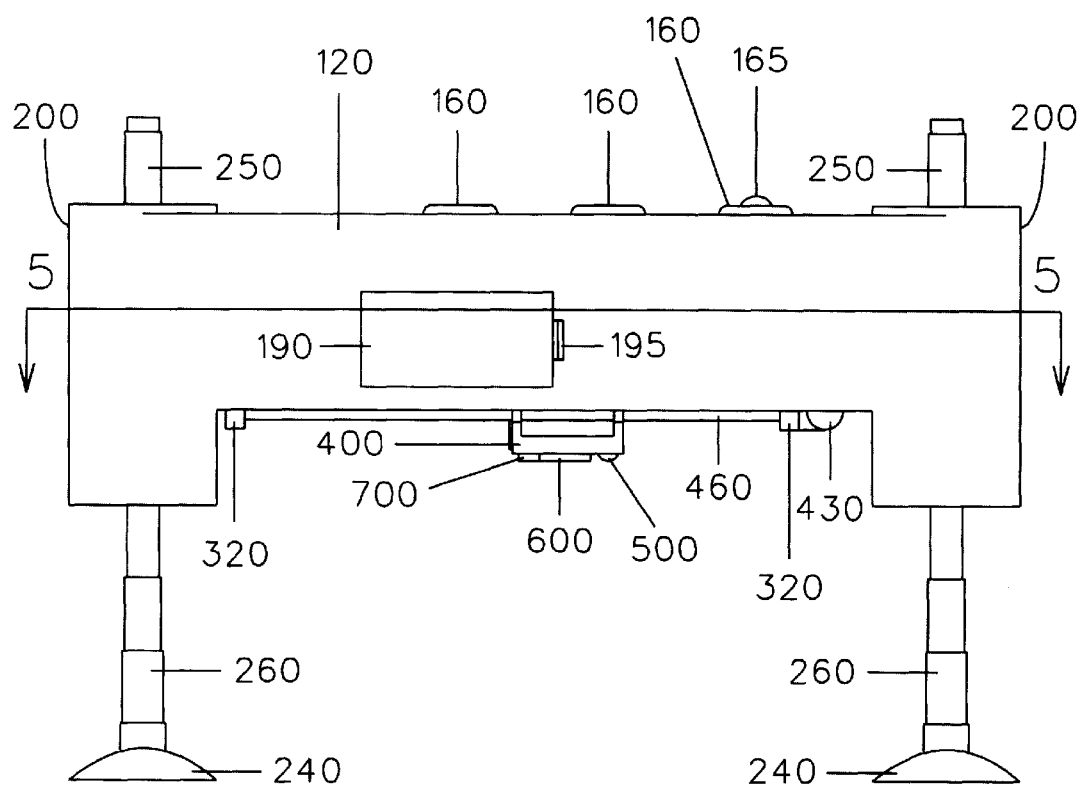
FIG. 2 is a right side view of the device of FIG. 1 in a partially lowered position.
Figure 3:
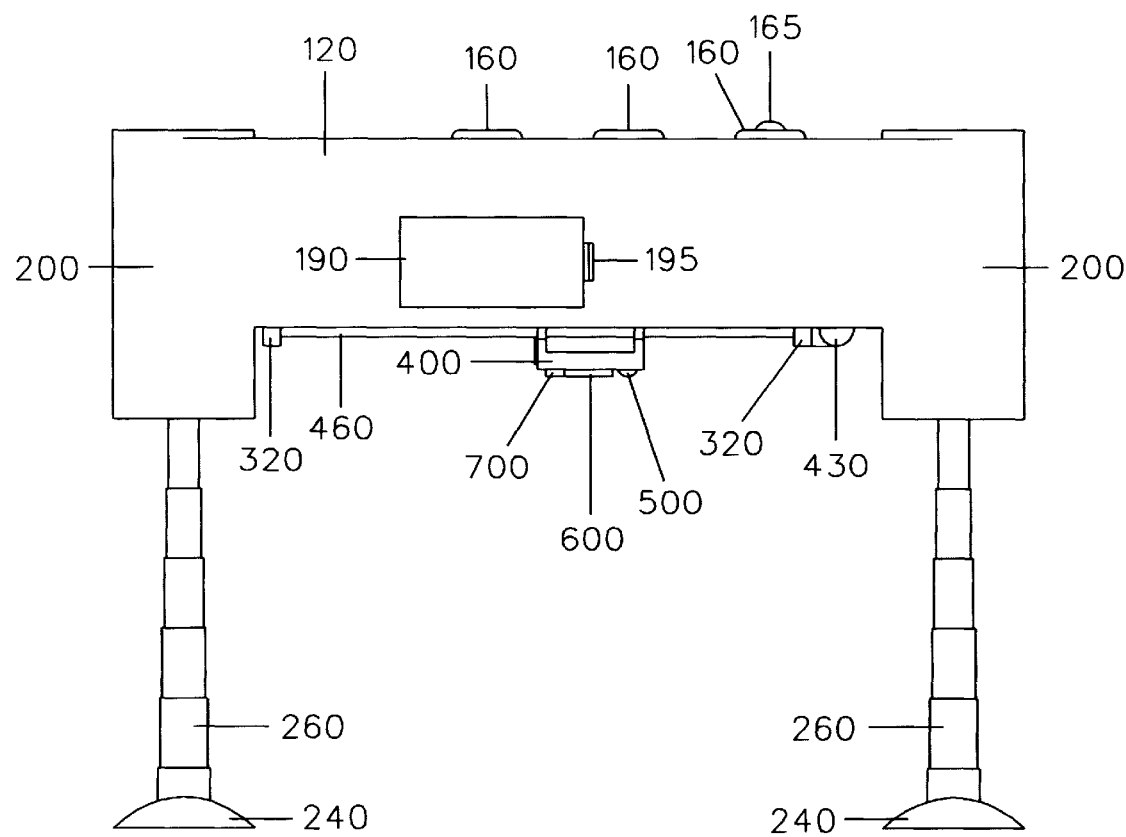
FIG. 3 is a right side view of the device of FIG. 1 in a fully raised position.
Figure 4:
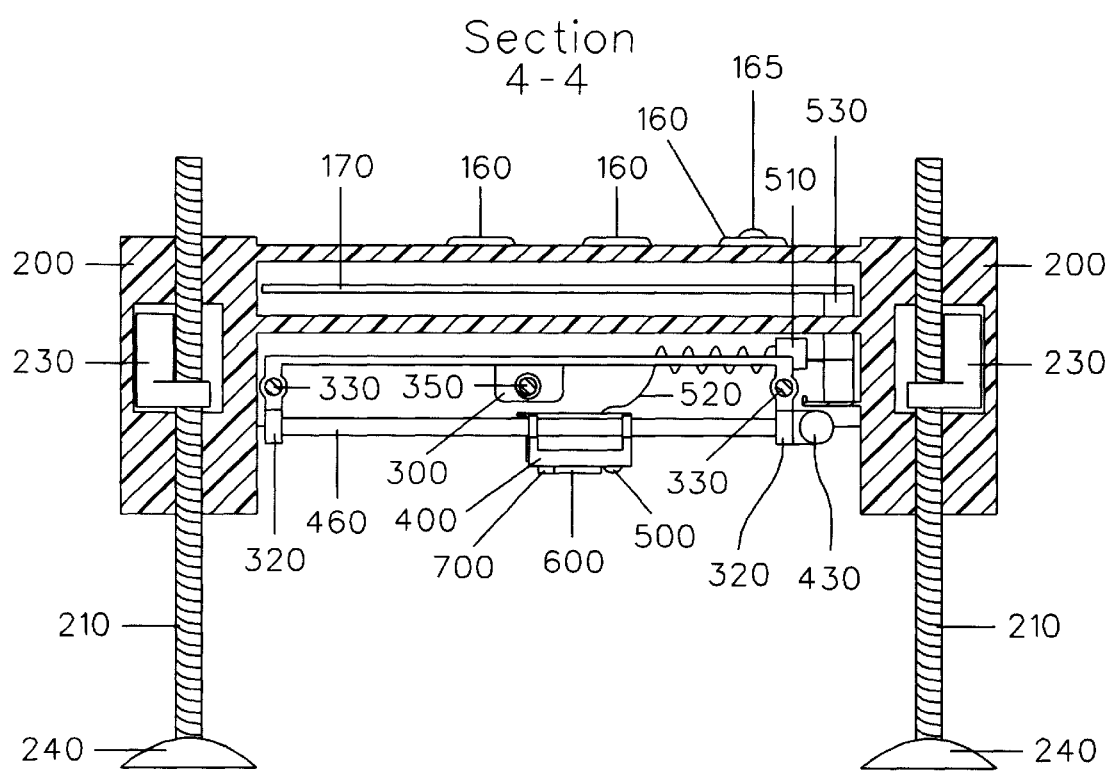
FIG. 4 is a sectional view taken along plane 4—4 in FIG. 1.

Turning more particularly to the drawings, FIGS. 1–3 show the now preferred embodiment of the improved device for locating and marking the position of blood vessels in a live human body. The device includes a generally rectangular housing 100 having a series of control buttons 160 mounted to a top surface 110 thereof. Each button 160 is linked to a central pr ocessing unit (CPU) 170 for communicating user requested functions thereto, the CPU being in the form of a printed circuit board mounted within the housing (FIG. 4). The top surface 110 further includes at least one light emitting diode (LED) 165 which lights up during sensor and plotting functions. Right 120 and left 130 side walls are normal to the top surface 110 of the housing 100 with spaced apart front 140 and rear 150 end walls intermediate the side walls 120, 130. A power cord 180 can be connected to an electrical outlet to thereby supply power to the device.

A series of upstanding cylindrical housings 200 are integrally attached to front 140 and rear walls 150, the housings being spaced apart immediately adjacent left and right side walls 130, 140 (FIG. 1). Each cylindrical housing 200 presents a threaded bore 220 for receiving a leg 210 therethrough, the leg having threads complementary to those within the bore 220 (FIG. 4). Each leg housing 200 further includes a motor 230 which can turn the leg 210 therein using gears or the like according to signals received from the CPU 170. Upon user selection of the height control function 160d, the CPU 170 will receive signals from a proximity sensor 500 (FIG. 9) regarding the distance between the housing 100 and a patient's skin as to be further described later. The CPU 170 will then activate each leg motor 230 to turn the legs 210 and thus raise or lower the housing 100 to a predetermined height above the patient's skin (FIGS. 2 and 3).

The lower end of each leg 210 is pivotally attached to a base 240 (FIGS. 1–3) such that the leg can rotate therein while the base remains in a fixed position. It is understood that each base 240 may be in the form of a suction cup so that the housing 100 will remain stationary during use when the base is fixed to a flat surface. Each leg 210 further includes upper 250 and lower 260 covers which telescopically extend over the threads of the leg 210 as the housing 100 is raised or lowered thereabout (FIGS. 2 and 3).

Figure 5:
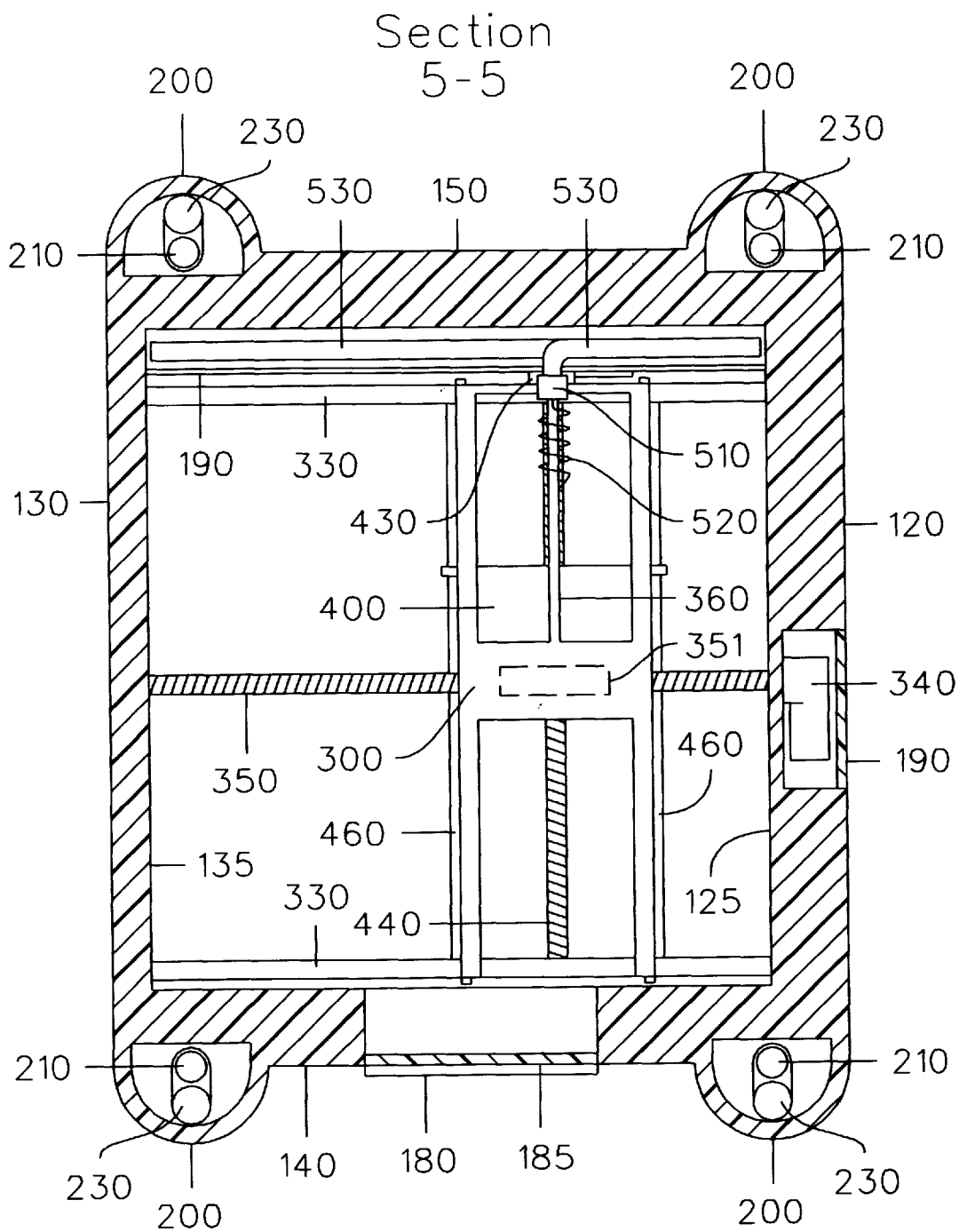
FIG. 5 is a top sectional view taken along plane 5—5 in FIG. 2 with the legs removed.
Figure 6:
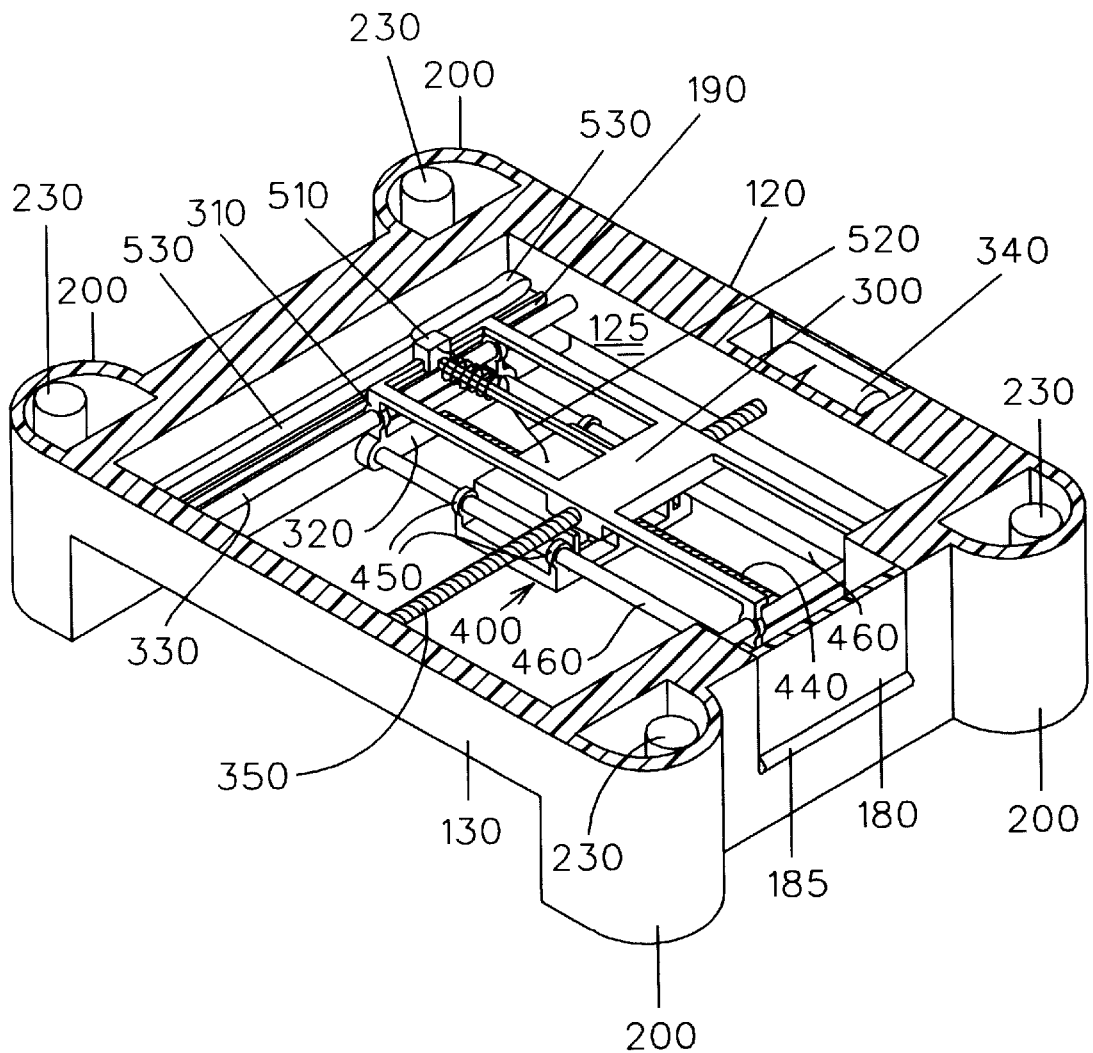
FIG. 6 is a perspective view of the device of FIG. 5.

As shown in FIGS. 5 and 6, the housing 100 includes an upper frame work including carriage 300 and a lower carriage 400 which cooperate to position the lower carriage over particular points about an x-y axis defined by the walls of the housing 100. The upper carriage 300 is movable in the x-direction while the lower carriage 400 is movable in the y-direction which is perpendicular to the x-direction. The upper carriage framework 300 is coupled 310 to oppositely disposed guide bars 330 mounted in extension along an interior surface of walls 140, 150 and is slidably movable therealong in the x-direction between the side walls 120, 130, the guide bars 330 being fixedly attached at their ends to inner surfaces 135, 125 of left 130 and right 120 side walls, respectively. A stepping motor 340 has a threaded shaft 350 extending therefrom which is rotatably mounted at the shaft 350 ends to the walls 125, 135. Motor 340 drives the shaft extending through a bore in the upper carriage. As the shaft 350 is rotated by the motor 340, the shaft 350 engages a gear or rack therein such as shown at 351. This engagement moves the carriage framework forward or backward in the x-direction along the shaft 350 and guide bars 330.

Figure 7:
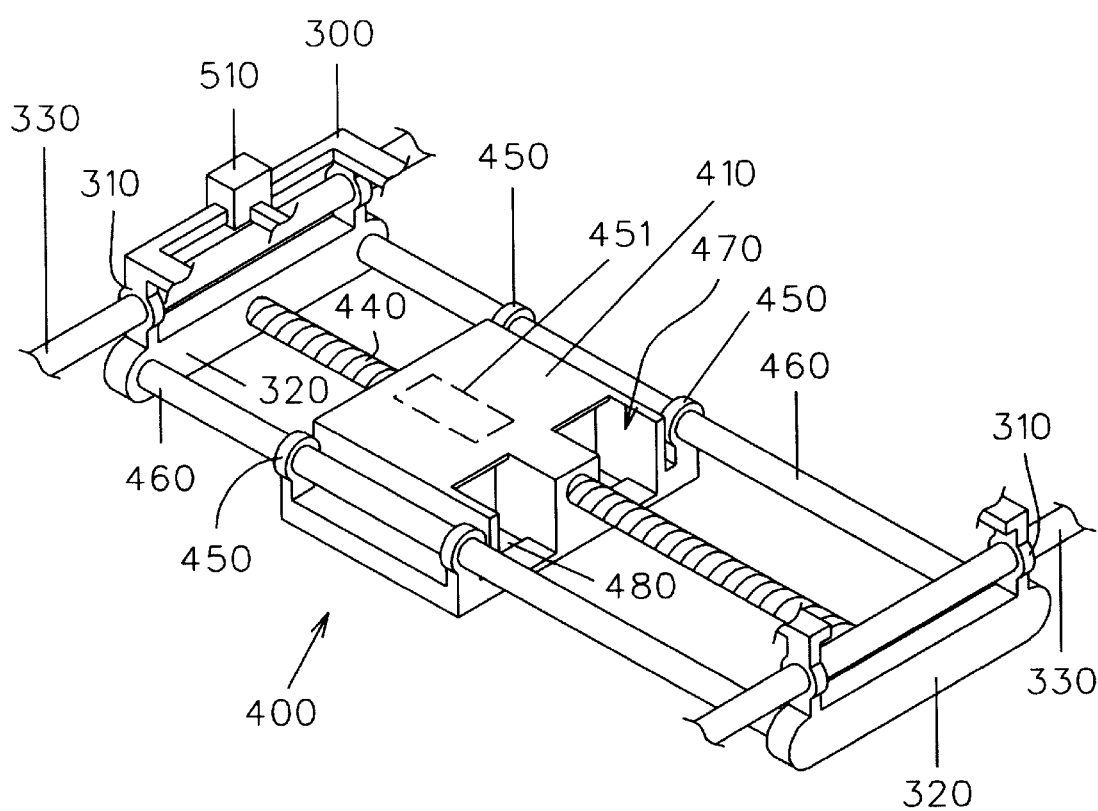
FIG. 7 is a perspective view of the lower carriage shown in FIG. 6 with ink cartridges removed.
Figure 8:
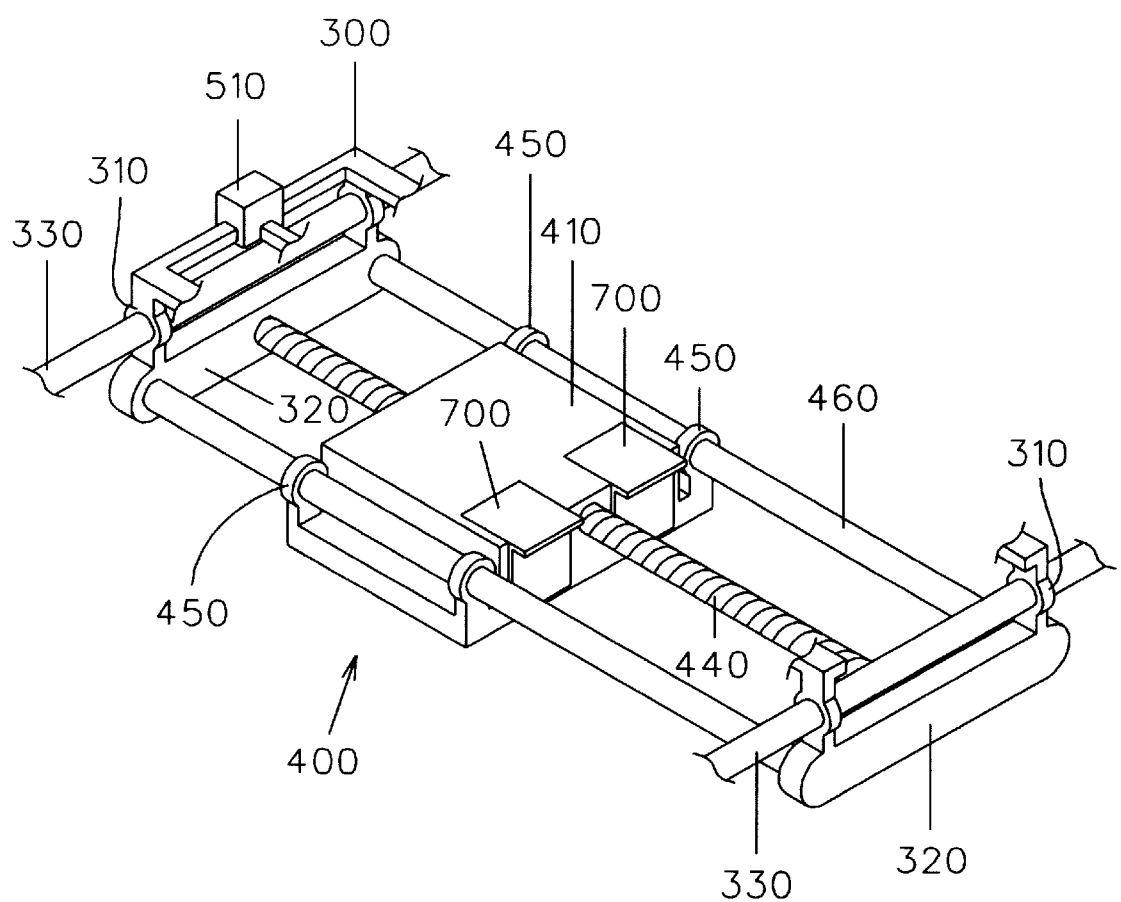
FIG. 8 is a perspective view of the lower carriage of FIG. 7 with the ink cartridges added.

The lower carriage 400 is similarly coupled 450 to a second pair of oppositely disposed parallel guide bars 460 which extend between walls 140, 150 below the first pair of guide bars 330 and perpendicular thereto. A second stepping motor 430 has a threaded shaft 440 extending therefrom. Shaft 440 is rotatably mounted at its ends between brackets 320. The shaft 440 rotatably extends through the lower carriage 440 and engages a gear or rack as shown as 351 therein. Accordingly, as motor 430 rotates shaft 440, carriage 400 will move back and forth therealong according to the direction of shaft 440 rotation. Couplings 310 further include a lower portion 320 integrally attached thereto, the lower portion 320 being fixedly attached to ends of the lower guide bars 460, shaft 440, and motor 430 (FIGS. 4, 7, and 8). The couplings 310 slide along the guide bars 330. Accordingly, the lower 400 carriage is linked to carriage 300 for movement in an x-direction upon movement of the upper carriage 300. However, since the lower carriage 400 can also move independently in the normal y-direction, the lower carriage 400 can be positioned above any particular x-y coordinate position.

The lower carriage 400 further includes a proximity sensor 500 fixedly attached to the bottom surface 420 thereof (FIG. 9), various types of proximity sensors being known in the art. By transmitting and receiving optical or ultrasonic signals, the sensor 500 can determine the distance between the housing 100 and a patient's skin such as an arm, leg or other body target area positioned beneath the housing 100. Signals from the proximity sensor 500 are transmitted to a junction box 510 through a wire 520 spirally secured about a strut 360 of the upper carriage (FIG. 6), the wire thus being extensible upon movement of the carriages. From the junction box 510, signals are transmitted through a ribbon cord 530 or another wire to the CPU 170. The ribbon cord 530 may rest upon a shelf 190 fixedly attached to the inner surface of the rear wall 150 of the housing 100. Upon user request, the CPU will activate the leg motors 230 to rotate the legs 210 so as to lower the housing 100 to a predetermined distance above the patient's skin.

A transducer assembly 600 is also fixedly attached to the bottom surface 420 of the lower carriage 400 adjacent the proximity sensor 500. The transducer 600 non-invasively transmits and receives ultrasonic sound waves for locating a blood carrying vessel beneath the patient's skin. It is understood that ultrasonic transducers are known in the art and may utilize the Doppler effect to enhance the accuracy of locating a vessel by detecting the flow of blood therein. According to the intensity of signals received by the transducer and subsequently transmitted to the CPU 170 through wires as described above, the CPU will activate the step motors 340, 430 to move upper 300 and lower 400 carriages about the x-y plane until a desired vessel position has been located. Positive location of a blood vessel is determinable by the CPU 170 according to predetermined levels of intensity of signals received by the transducer 600.

When a blood vessel has been located, the CPU 170 causes the x-y coordinates thereof to be stored in a memory location. The CPU 170 then directs the carriages 300, 400 to continue moving within the x-y plane such that the strength of the ultrasonic signals are maintained within a predetermined range, thus causing the vessel to be tracked throughout the plane. As the vessel is tracked, the x-y coordinates are stored in sequential memory locations. If the strength of the signal received by the transducer 600 exceeds a predetermined acceptable variation or a boundary of the x-y plane is reached as defined by the housing walls, the vessel sensing function is discontinued.

Figure 9:
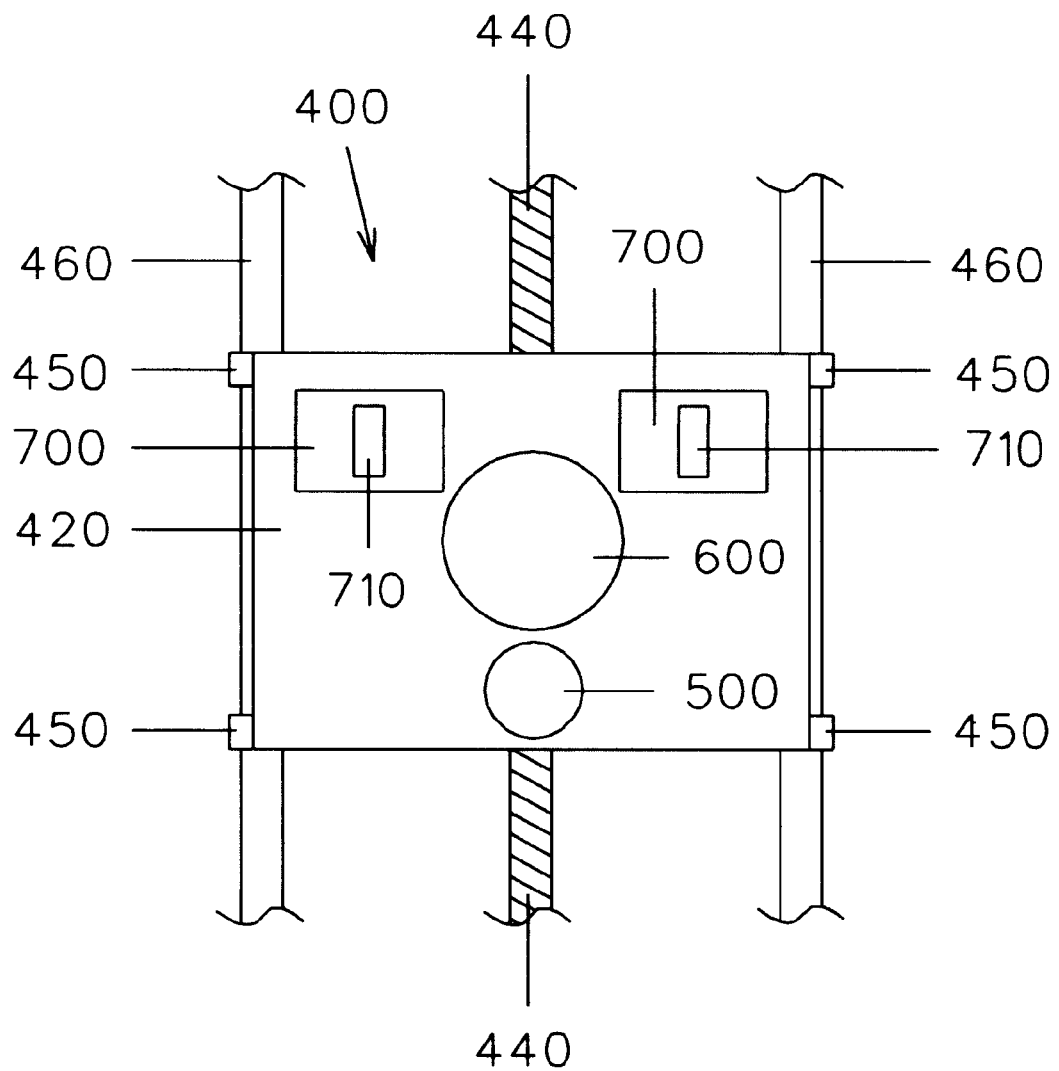
FIG. 9 is a fragmentary bottom view of the lower carriage of FIG. 8.
Figure 10:
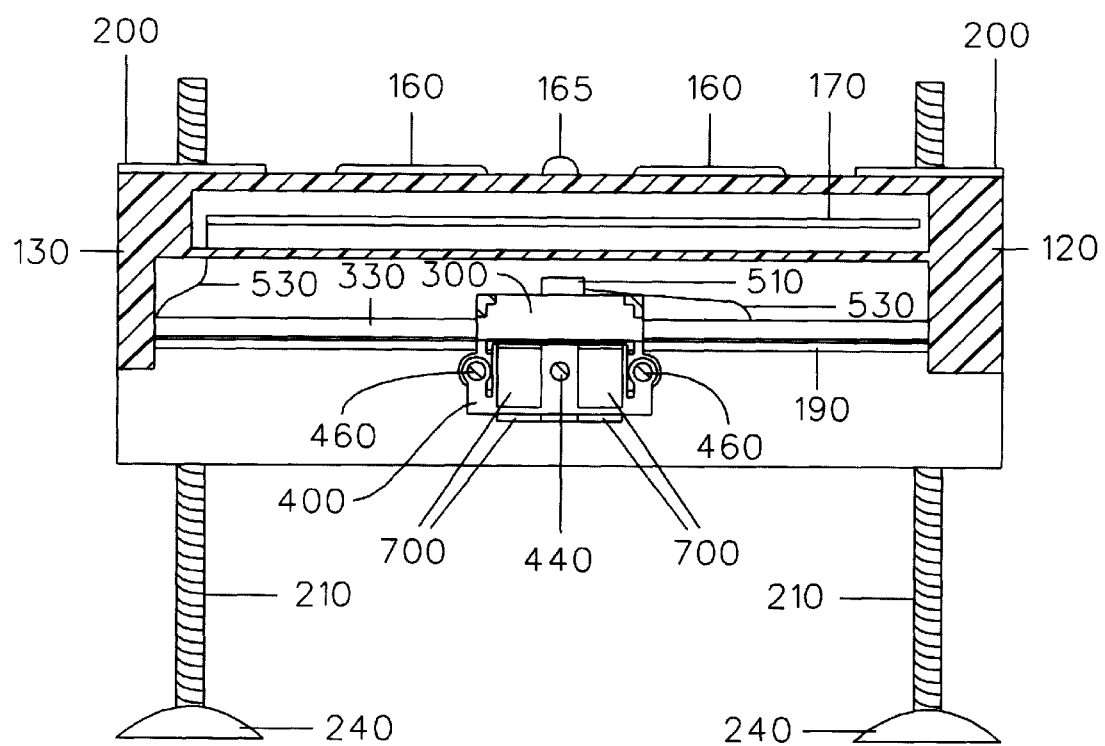
FIG. 10 is a sectional view of the device taken along plane 10—10 of FIG. 1.
Figure 11:
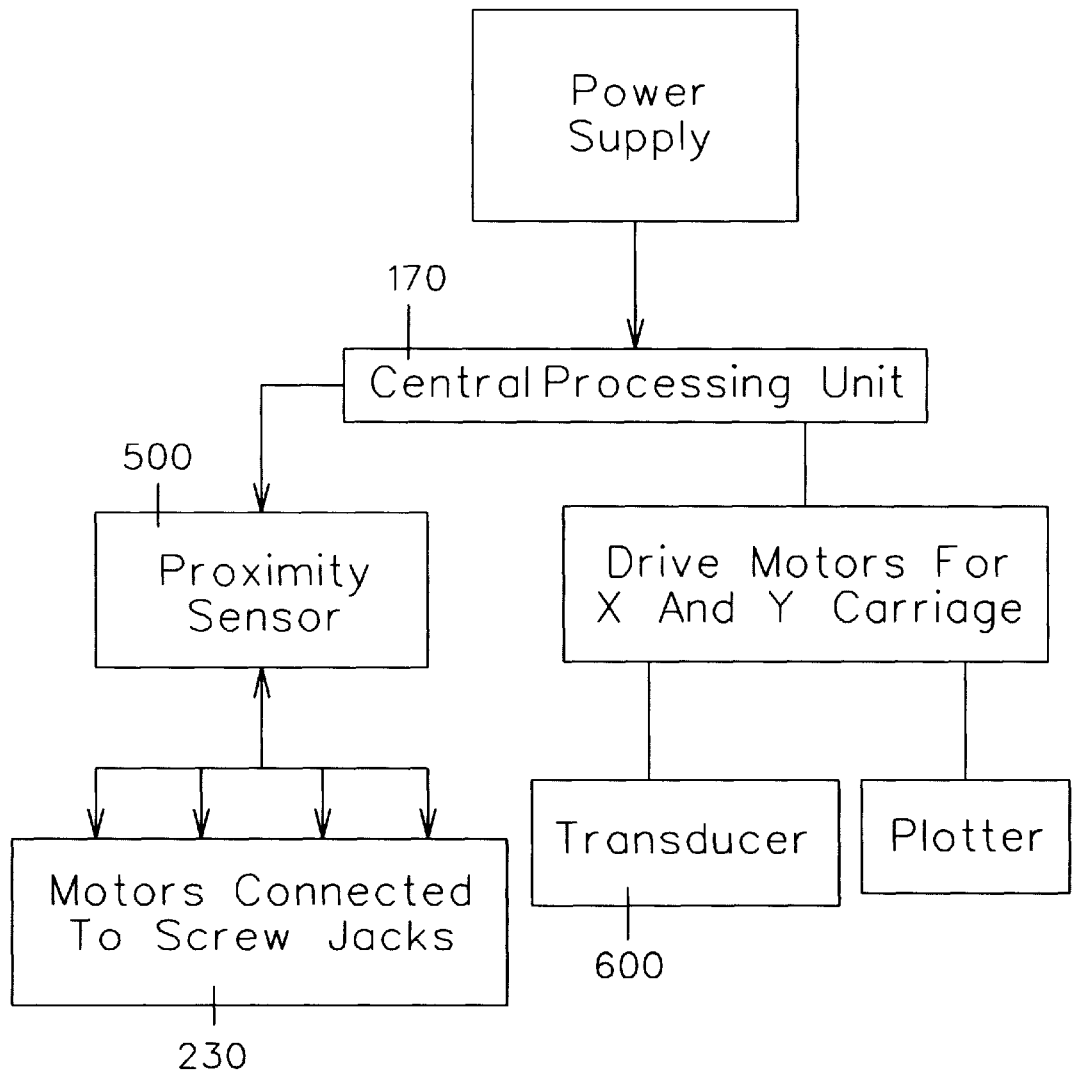
FIG. 11 is a block diagram of the operation of the device of FIG. 1.

A pair of spaced apart cavities 470 are presented in the upper surface 410 of the lower carriage 400 for receiving a pair of ink cartridges 700 therein (FIG. 7). Each cartridge 700 is preferably of the ink-jet type which is known in the art. The bottom surface 420 of the lower carriage 400 presents apertures 480 through which ink ejection heads 710 of the ink cartridges 700 may extend for ejecting ink against the skin of a patient as controlled by the CPU (FIGS. 7 and 9).

Upon a user request to plot a vessel which has been located and tracked by the transducer 600, the CPU 170 will activate the carriages 300, 400 to move along the x-y coordinates previously stored in sequential memory locations. Simultaneously, the ejection heads 710 of the ink cartridges 700 will mark the skin of the body part of the patient overlying the blood vessel. Alternatively, the marking can be done during vessel tracking. It should be understood that the spaced apart ink cartridges 700 allow a vessel to be plotted within each boundary of the x-y plane as defined by the housing walls. It is further understood that while the peripheral boundaries of a vessel may be marked so as to enhance the accuracy of ultimate needle penetration, the dual ink cartridge configuration does not necessarily plot the boundaries simultaneously.

The housing 100 provides access to internal components. As particularly shown in FIGS. 1 and 6, a first door 180 is hingedly 185 mounted to the front 140 and top 110 walls for providing user access to the lower carriage 400 for replacing ink cartridges 700. The door 180 includes a window 182 for user viewing of the components within the housing 100. A second access door 190 is mounted to the right side wall 120 for user access to the stepping motor 340 which drives the upper carriage 300. The second door 190 includes a flange 195 which may be depressed by a user to release the door from the wall 120.

Accordingly, it can be seen that the present invention provides a self-contained, portable device which non-invasively locates the position of a blood carrying vessel within the x-y plane of the device housing. In addition, the device can be utilized with various transducer and control assemblies so as to automatically plot one or more locations of peripheral boundaries of the vessel onto the skin of the patient. The device can remain stationary while the above described functions are accomplished under the control of a central processing unit.

It is understood that while certain forms of this invention have been illustrated and described, it is not limited thereto except insofar as such limitations are included in the following claims and allowable functional equivalents thereof.

Having thus described the invention, what is claimed as new and desired to be secured by letters patent is as follows:

1. A device for locating a blood vessel within a human body comprising:

a housing having front and rear walls and a pair of side walls extending therebetween;

means for positioning said housing at a selected position over a portion of a human body;

a transducer assembly adapted to project ultrasonic signals towards a selected portion of the body and adapted to utilize said projected signals to detect a blood vessel location underlying a body portion and produce signals corresponding thereto, said signals providing data to the control assembly coupled to said transducer assembly for processing, said control assembly adapted to process the data for presenting control signals corresponding to a location of the selected blood vessel;

a carriage for said transducer assembly;

first means responsive to said control signals for moving said carriage to a first position between said side walls;

second means responsive to said control signals for moving said carriage to a second position between said front and rear walls relative to said first position, said first and second moving means positioning said carriage to the location of the blood vessel positioned adjacent said housing.

2. The device as claimed in claim 1 further comprising means on said carriage for marking on the body portion the location of the blood vessel.

3. The device as claimed in claim 1 wherein said marking means comprises an ink reservoir on said carriage adapted to respond to a signal from the control assembly to discharge ink from the reservoir on the human body portion therebelow, said ink marking a blood vessel location.

4. The device as claimed in claim 1 wherein said first moving means comprises:

a first guide means for providing a course along said front wall;

a second guide means for providing a course along said rear wall;

a first bracket coupled to said first guide means;

a second bracket coupled to said second guide means;

framework extending between said first and second brackets;

means for coupling said carriage to said framework;

means for driving said brackets in back and forth movement along said first and second guide means, whereby to move said framework and carriage coupled thereto in back and forth movement between said side walls.

5. The device as claimed in claim 4 wherein said bracket drive means comprises:

a shaft having first and second ends rotatably mounted to said side walls, said shaft extending between said side walls and through said framework;

means on said framework for engaging said shaft;

means for rotating said shaft in first and second directions, a rotation of said shaft in a first direction causing said engaging means to move said framework and brackets towards one of said side walls, a movement of said shaft in an opposed second direction causing said engaging means to move said framework and brackets towards the other of said side walls.

6. The device as claimed in claim 4 wherein said second moving means comprises:

third and fourth guide means for providing courses extending between said first and second brackets;

a third bracket connected to said carriage and slidable along said third guide means;

a fourth bracket connected to said carriage and slidable along said fourth guide means;

a second shaft extending between said first and second brackets, said second shaft having first and second ends rotatably mounted to said first and second brackets and movable therewith;

means in said carriage for engaging said second shaft; and means for rotating said second shaft in first and second directions, a rotation in a first direction engaging said carriage engaging means to move said carriage in a first direction towards said front wall, a rotation of said shaft in a second direction causing said carriage engaging means to move said carriage in a second direction towards said rear wall.

7. The device as claimed in claim 6 wherein said positioning means comprises:

a plurality of support columns depending from said housing, said columns having a base for contact with a support surface, said columns depending from said housing to space said housing away from the support surface with the body portion positioned between said housing and the support surface.

8. The device as claimed in claim 7 further comprising:

a plurality of threads on said columns;

means in said housing for engaging said threadable columns, whereby a rotation of said columns in one direction increases the length of said columns depending from said housing to raise the height of said housing relative to the support surface, a rotation of said columns in an opposed direction decreasing the length of said columns depending from said housing to decrease the height of said housing relative to the support surface.

9. For use with a control assembly adapted to produce a control signal in response to a signal generated by a transducer assembly corresponding to a blood vessel location underlying a portion of the human body comprising:

a housing;

means for positioning said housing at a selected position adjacent a portion of a human body;

a carriage assembly adapted to support the transducer assembly;

first means responsive to the control signal for mounting said carriage assembly to said housing in lateral movement relative to said housing;

second means responsive to the control signal for moving said carriage assembly in longitudinal movement relative to said housing, said first and second mounting means positioning said carriage along said housing at a position relative to the location of the blood vessel corresponding to the signal generated by the transducer assembly.

10. The device as claimed in claim 9 further comprising means on said carriage for marking on the body portion the location of the blood vessel.

11. The device as claimed in claim 9 wherein said first moving means comprises:

a first guide laterally extending along said housing;

a second guide laterally extending along said housing;

a first bracket slidably coupled to said first guide;

a second bracket slidably coupled to said second guide;

framework extending between said first and second brackets and slidable therewith;

said carriage assembly linked to said framework;

means for driving said brackets in back and forth movement along said first and second guides, whereby to move said framework and carriage assembly coupled thereto in lateral movement relative to said housing.

12. The device as claimed in claim 11 wherein said bracket drive means comprises:

a shaft rotatably mounted to said housing, said shaft laterally extending along said housing and through said framework;

means on said framework for engaging said threaded shaft;

means for rotating said shaft in first and second directions, a movement of said shaft in a first direction causing said engaging means to move said framework in a first direction along said guides, a movement of said shaft in an opposed direction causing said engaging means to move said framework in a second opposed direction along said guides.

13. The device as claimed in claim 11 wherein said second moving means comprises:

third and fourth guides extending between said first and second brackets;

a third bracket connected to said carriage and slidable along said third guide;

a fourth bracket connected to said carriage and slidable along said fourth guide;

a second shaft rotatably mounted to said housing and longitudinally extending along said housing;

means in said carriage assembly for engaging said second shaft; and means for rotating said second shaft in first and second directions, a rotation in a first direction engaging said carriage assembly engaging means to move said carriage assembly in a first direction along said third and fourth guides, a rotation of said shaft in a second direction engaging said carriage engaging means to move said carriage assembly in a second opposed direction along said third and fourth guides.

14. The device as claimed in claim 9 wherein said positioning means comprises:

a plurality of columns depending from said housing, said columns having a base for contact with a support surface, said columns depending from said housing at a selectable length to space said housing away from the support surface, the body positioned between said housing and the support surface.

15. A device for locating a blood vessel within a human body comprising:

a housing adapted to be positioned adjacent a selected portion of a human body;

a transducer assembly adapted to project signals towards a selected portion of the body and adapted to utilize said projected signals to produce signals indicative of a blood vessel location underlying the body portion, said produced signals providing data to the control assembly coupled to said transducer assembly for processing, said control assembly adapted to process the data for presenting control signals corresponding to a location of the selected blood vessel;

a framework assembly;

means responsive to said control signals for moving said framework assembly in a first back and forth movement relative to said housing;

a carriage assembly;

means for connecting said carriage assembly to said framework for movement therewith;

means responsive to said control signals for moving said carriage in a second back and forth movement relative to said housing generally normal to said first back and forth movement, said framework and carriage moving means positioning said carriage at the location of the selected blood vessel.

16. The device as claimed in claim 15 further comprising means on said carriage for marking on the body portion the location of the selected blood vessel.

17. The device as claimed in claim 13 wherein said marking means comprises an ink reservoir on said carriage adapted to respond to a signal from the control assembly to discharge ink from the reservoir on the human body portion therebelow, said ink marking a blood vessel location.

18. The device as claimed in claim 17 wherein said framework moving means comprises:

first guide means for providing a course in first and second opposed directions along said housing corresponding to said first back and forth movement;

said framework coupled to said first guide means;

means for driving said framework in back and forth movement along said first guide means, whereby to move said framework and carriage assembly coupled thereto in back and forth movement along said guide means.

19. The device as claimed in claim 18 wherein said framework drive means comprises:

a shaft having first and second ends rotatably mounted to said housing, said shaft extending through said framework;

means on said framework for engaging said shaft;

means for rotating said shaft in first and second directions, a rotation of said shaft in a first direction causing said framework engaging means to move said framework in a first direction along said first guide means, a rotation of said shaft in an opposed second direction causing said framework engaging means to move said framework in a second direction along said first guide means.

20. The device as claimed in claim 18 wherein said second moving means comprises:

second guide means for providing a course in third and fourth opposed directions along said housing and generally normal to said first and second directions;

said carriage assembly coupled to said second guide means;

a second rotatable shaft extending along said third and fourth opposed directions, said second shaft movable with said framework;

means in said carriage assembly for engaging said second shaft; and means for rotating said second shaft in first and second directions, a rotation of said second shaft in a first direction engaging said carriage engaging means to move said carriage assembly in a third direction along said housing, a rotation of said second shaft in a second direction causing said carriage assembly engaging means to move said carriage in a fourth opposed direction along said housing.

* * * * *